US008556876B2

(12) United States Patent
Molander et al.

(10) Patent No.: US 8,556,876 B2
(45) Date of Patent: Oct. 15, 2013

(54) PERSONAL CARE ARTICLES OF COMMERCE COMPRISING A MAGNETIC MEMBER

(75) Inventors: John Carroll Molander, Montgomery, OH (US); Mark James Kline, Okeana, OH (US); Daniel Charles Peck, Mason, OH (US); Tracey Elaine Beckman, Mason, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 1565 days.

(21) Appl. No.: 11/448,473

(22) Filed: Jun. 7, 2006

(65) Prior Publication Data

US 2006/0287634 A1 Dec. 21, 2006

Related U.S. Application Data

(60) Provisional application No. 60/692,645, filed on Jun. 21, 2005.

(51) Int. Cl.
*A61F 13/56* (2006.01)

(52) U.S. Cl.
USPC ..................... 604/386; 604/385.01

(58) Field of Classification Search
USPC .............................. 604/358, 391; 428/99, 900
See application file for complete search history.

(56) References Cited

U.S. PATENT DOCUMENTS

| | | | |
|---|---|---|---|
| 3,326,399 A * | 6/1967 | Ausnit | 215/3 |
| 3,730,804 A * | 5/1973 | Dickey | 156/272.4 |
| 4,200,547 A | 4/1980 | Beck | |
| 4,941,236 A | 7/1990 | Sherman et al. | |
| 5,103,501 A | 4/1992 | Meisels | |
| 5,151,092 A | 9/1992 | Buell et al. | |
| 5,545,157 A | 8/1996 | Van Iten | |
| 5,558,662 A | 9/1996 | Van Iten | |
| 5,609,788 A | 3/1997 | Deetz | |
| 5,704,480 A | 1/1998 | Scholz et al. | |
| 5,833,594 A | 11/1998 | Hsieh | |
| 5,843,329 A | 12/1998 | Deetz | |
| 5,897,542 A * | 4/1999 | Lash et al. | 604/378 |

(Continued)

FOREIGN PATENT DOCUMENTS

| | | |
|---|---|---|
| DE | 20018405 U1 | 2/2001 |
| EP | 1 444 907 A1 | 8/2004 |

(Continued)

OTHER PUBLICATIONS

International Search Report.

*Primary Examiner* — Susan Su
(74) *Attorney, Agent, or Firm* — Abbey A. Lopez; Laura L. Whitmer

(57) ABSTRACT

A personal care article including a thermoplastic magnetic member. The thermoplastic magnetic member is formed of a thermoplastic material with magnetic particles dispersed therethrough. The thermoplastic material comprises a resin selected from the group consisting of polyolefins, thermoplastic elastomers, polyamides, polyacetals, polyethers, polyesters, polyurethanes, poly(meth)acrylates, and compatible mixtures thereof. The magnetic particles are selected from the group consisting of magnetoplumbite-structure ferrite particles, rare-earth magnet particles, and mixtures thereof. The thermoplastic material may be disposed on a surface of a fibrous substrate. A surface of the thermoplastic magnetic member may be profiled. A second thermoplastic magnetic member may have an opposite magnetic polarity and a complementary surface profile such that the two thermoplastic magnetic members may be magnetically joined and mechanically interlocked when in a mated configuration.

5 Claims, 5 Drawing Sheets

(56) References Cited

U.S. PATENT DOCUMENTS

| | | | |
|---|---|---|---|
| 6,312,795 | B1 | 11/2001 | Yamamoto |
| 6,436,520 | B1 | 8/2002 | Yamamoto |
| 6,460,230 | B2* | 10/2002 | Shimamura et al. ............ 24/452 |
| 6,463,635 | B2* | 10/2002 | Murasaki ........................ 24/452 |
| 6,547,436 | B2 | 4/2003 | Sutton |
| 6,749,551 | B2 | 6/2004 | Metzler et al. |
| 6,836,899 | B1 | 1/2005 | Glasmire |
| 7,322,967 | B2* | 1/2008 | Kondo ..................... 604/385.29 |
| 7,431,976 | B2* | 10/2008 | Hermann et al. ............. 428/100 |
| 2001/0038161 | A1 | 11/2001 | Kenney et al. |
| 2002/0022820 | A1 | 2/2002 | Kline et al. |
| 2002/0058123 | A1* | 5/2002 | Kenney et al. ................... 428/99 |
| 2002/0076520 | A1* | 6/2002 | Neeb et al. ..................... 428/100 |
| 2002/0082537 | A1 | 6/2002 | MacAllister |
| 2002/0164451 | A1* | 11/2002 | Fujisawa et al. .............. 428/100 |
| 2003/0099811 | A1* | 5/2003 | Poulakis ........................ 428/126 |
| 2003/0214068 | A1* | 11/2003 | Fujisawa et al. .............. 264/145 |
| 2004/0122399 | A1* | 6/2004 | McDaniel ................ 604/385.02 |
| 2004/0199092 | A1 | 10/2004 | Biewend et al. |
| 2004/0206638 | A1 | 10/2004 | Metzler et al. |
| 2004/0222553 | A1 | 11/2004 | Desai et al. |
| 2004/0256340 | A1 | 12/2004 | Clark et al. |
| 2005/0015069 | A1 | 1/2005 | Hamilton et al. |
| 2005/0137553 | A1* | 6/2005 | Bechyne et al. ......... 604/385.02 |
| 2006/0142720 | A1* | 6/2006 | Zander et al. ............ 604/385.02 |
| 2007/0049891 | A1* | 3/2007 | Clark et al. .............. 604/385.13 |
| 2009/0013506 | A1* | 1/2009 | Mizuhara et al. ............... 24/442 |

FOREIGN PATENT DOCUMENTS

| | | |
|---|---|---|
| FR | 2 764 297 A1 | 12/1998 |
| JP | 9215710 A | 8/1997 |
| JP | 2002309401 A | 10/2002 |
| JP | 2004194641 A | 7/2004 |
| KR | 2003046142 A | 6/2003 |
| WO | WO 01/60214 A2 | 8/2001 |

* cited by examiner

PERSONAL CARE ARTICLES OF COMMERCE COMPRISING A MAGNETIC MEMBER

CROSS REFERENCE TO RELATED APPLICATION

This application claims the benefit of U.S. Provisional Application No. 60/692,645, filed Jun. 21, 2005.

FIELD OF THE INVENTION

The present invention relates to articles of commerce comprising at least one personal care article and a package therefor where at least one of the personal care article and the package comprises a thermoplastic magnetic member. In preferred embodiments, the thermoplastic magnetic member has a three dimensional profile which enables a matched pair of the thermoplastic magnetic members to both magnetically and mechanically interact.

BACKGROUND OF THE INVENTION

Magnetic materials, including magnetic materials comprising a thermoplastic, are well known. One use of such materials is as a part of a closure system (e.g., a woman's purse with a magnetic catch). Typically, such magnetic materials in conventional closure systems are in the form of rigid metal magnets or flexible magnetic tapes that are attached to articles through various mechanical and/or adhesive means. See, for example, U.S. Pat. Nos. 4,200,547 and 6,312,795 and published U.S. Pat. No. 6,749,551 and US 2005/0015069.

Such closure systems have various problems with respect to use in a personal care article. For example, the cost of the equipment necessary to position, attach (and, if necessary, cut) a flexible, bonded magnetic material to the product can be excessive. Further, such magnetic materials are limited in shape availability or other desirable properties for use in a personal care article. For example, metallic magnets are available in many shapes but are relatively expensive, particularly for application to a single use personal care article. Further, such metallic magnets have limited mechanical flexibility which is also desirable for many personal care articles.

On the other hand, flexible materials of the art are typically manufactured using a calendering process or extruded in a ribbon form. As will be recognized, such processes result in a substantially planar two dimensional form for the flexible magnetic materials. As will also be recognized, such a two dimensional form can be cut into a shaped configuration by known methods, such as die cutting. However, since the magnetic material is formed in a separate step such material, even if it is somewhat flexible still needs to be applied to a substrate for use in many personal care articles. As is well known, the apparatus (e.g., cut and slip technology) for such application for single use personal care articles is both mechanically complex and expensive. It is also necessary to provide means (e.g., an adhesive) to attach the magnetic material to the substrate.

Three dimensional structures are also known where a polymer magnetic particle blend is injection molded to form an article. However, such preformed structures also must be placed and adhered to a substrate using additional manufacturing steps similar to those discussed above for application of flexible magnetic materials.

Printing magnetic materials is also known. However, such printed materials are said to comprise a magnetic ink where magnetic particles are dispersed in a vehicle and printed onto a substrate using known techniques such as screen printing. As will be recognized printing processes carry the burden of environmental undesirability due to the generation of volatile organic carbon and other effluents. Also, the presence of a vehicle limits the concentration of magnetic particles that may be incorporated into the ink due to the increase in viscosity as solids level increases with the resulting need to provide enough vehicle to maintain a printable composition because, as will be recognized, the vehicle is then evaporated in a separate drying/curing step.

Thus there is a need for improved personal care articles and articles of commerce comprising such personal care articles in suitable packaging where either the personal care article or the packaging is provided with a magnetic feature.

There is a further need for magnetic features with a high magnetic flux density that can be applied to a substrate using relatively simple process apparatus such a printing.

There is still a further need for flexible magnetic features that have a relatively complex three dimensional configuration so as to provide added benefits to users of personal care articles such as improved conformity to an underlying complex three dimensional shape or mechanical interlocking of a matched pair of magnetic elements.

SUMMARY OF THE INVENTION

In one embodiment the present invention comprises a personal care article of commerce, where the article of commerce comprises at least one personal care article and a package therefor. The article of commerce also comprises a thermoplastic magnetic member which comprises a thermoplastic material with magnetic particles dispersed therethrough. The thermoplastic material comprises a resin selected from the group consisting of polyolefins, thermoplastic elastomers, polyamides, polyacetals, polyethers, polyesters, polyurethanes, poly(meth)acrylates; and compatible mixtures of more than one thermoplastic material and the magnetic particles are selected from the group consisting of magnetoplumbite-structure ferrite particles and rare-earth magnet particles and mixtures of magnetic particle types.

A second embodiment of the present invention is a thermoplastic magnetic member having a three dimensional profile. The thermoplastic magnetic member comprises the same material as the thermoplastic magnetic member described above and has two surfaces where each point on the second surface is separated from a vertically opposed point on the first surface by a z-dimension and there is at least one position on the second surface where the z-dimension differs from the z-dimension of a different position on the second surface.

In a third embodiment of the present invention a thermoplastic magnetic member that comprises the same material as the thermoplastic magnetic member described above is disposed on the surface of a fibrous substrate and at least a portion of the thermoplastic material penetrates beneath the surface by at least about two fiber diameters.

BRIEF DESCRIPTION OF THE DRAWINGS

While the specification concludes with claims particularly pointing out and distinctly claiming the subject matter which is regarded as the present invention, it is believed that the invention will be more fully understood from the following description taken in conjunction with the accompanying drawings, in which:

DETAILED DESCRIPTION OF THE INVENTION

Definitions

Figures 1, 2:
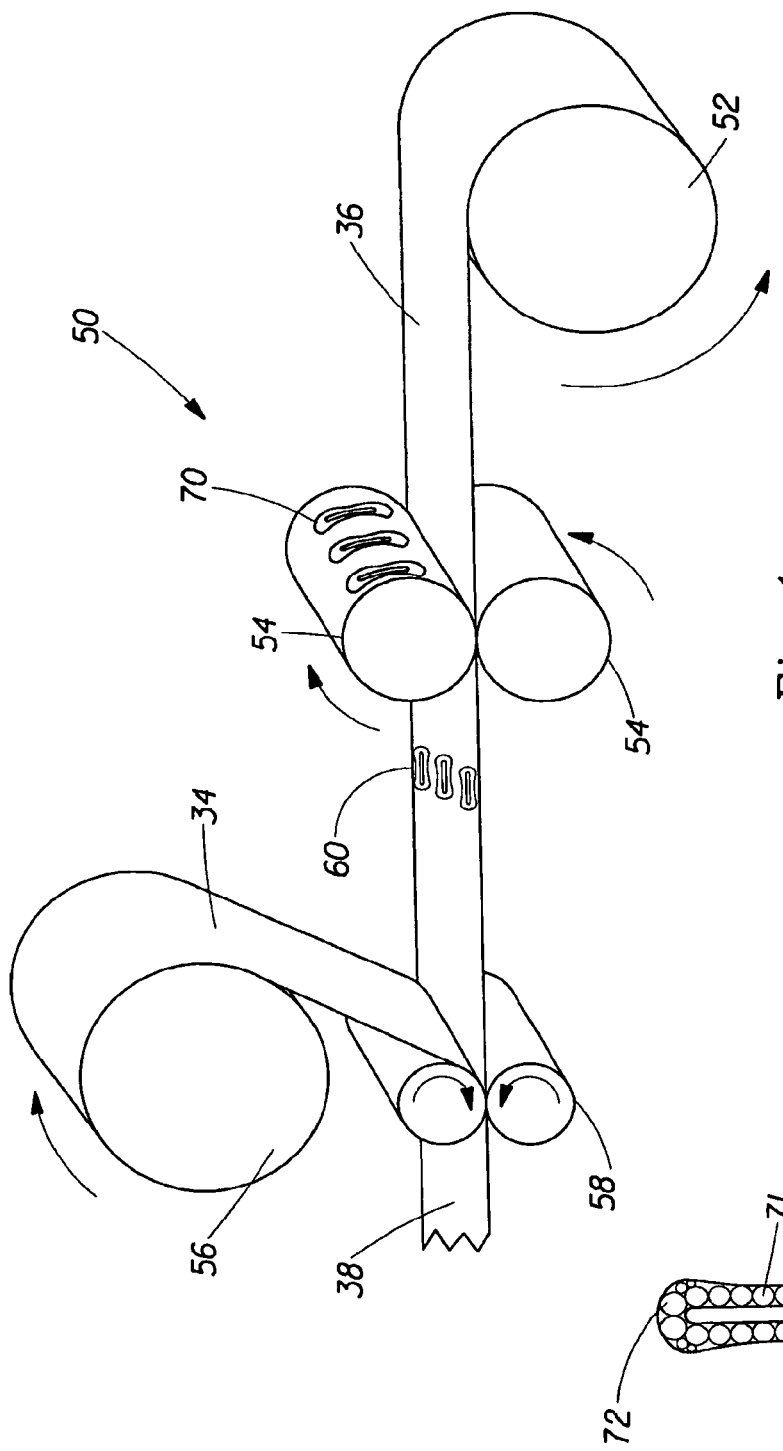
FIG. 1 is a schematic view of a process for manufacture of a thermoplastic magnetic material according to the present invention.
FIG. 2 is an enlarged view of a portion of FIG. 1.

The term "article" refers herein to both disposable and durable articles.

The term "disposable" is used herein to describe products which generally are not intended to be laundered or otherwise restored or extensively reused in their original function, i.e., they are intended to be discarded after fewer than about 10 uses, preferably after fewer than about 5 uses or even after a single use. It is preferred that such disposable articles be recycled, composted or otherwise disposed of in an environmentally compatible manner.

The term "durable" is used herein to describe products which generally are intended to be laundered or otherwise restored or extensively reused in their original function, i.e., preferably they are intended to be used more than about 10 times.

The term "disposable absorbent article" refers herein to a device that normally absorbs and retains fluids. In certain instances, the phrase refers to devices that are placed against or in proximity to the body of the wearer to absorb and contain the excreta and/or exudates discharged from the body, and includes such personal care articles as baby diapers, baby training pants, adult incontinence articles, feminine hygiene articles, baby swim diapers, wound dressings, and the like. In other instances, the phrase refers to protective articles, such as, for example, dining bibs that have the ability to absorb food items to prevent staining of the wearer's clothing.

The term "diaper" refers herein but is not limited to baby diapers, baby training pants, disposable baby swim wear, and adult incontinence articles and refers to a disposable fluid-handling article generally worn by infants and other incontinent persons about the lower torso.

The term "feminine hygiene articles" refers herein to any absorbent article worn by women to absorb and contain menses and other vaginal exudates.

The term "body wrap" refers herein to an article or a garment worn about the body, typically to provide some therapeutic benefit, such as, for example, pain relief, wound coverage or for holding another device or article near the body.

The term "personal care article" refers herein to articles intended to facilitate the care of an individual and includes but is not limited to diapers, wet wipes, feminine hygiene articles and body wraps.

The term "web" refers herein to any continuous material, including a film, foil, a non-woven fabric, a woven fabric, a foam or a combination thereof, or a cellulosic material including wood pulp, and the like, having a single layer or multiple layers.

The term "substrate" refers herein to any material, including a film, a foil, a non-woven fabric, a woven fabric, a foam or a combination thereof, or a cellulosic material including wood pulp, and the like, having a single layer or multiple layers, and suitable for application of a polymeric material on at least one surface of the "substrate."

The term "fibrous substrate" refers herein to a material comprised of a multiplicity of fibers that could be either a natural or synthetic material, metallic, or any combination thereof, for example nonwoven materials, woven materials, knitted materials, cellulosic materials, and any combinations thereof.

The term "non-woven" refers herein to a fabric made from continuous filaments and/or discontinuous fibers, without weaving or knitting, by processes such as carding, spun-bonding and melt-blowing. The non-woven fabric can comprise one or more non-woven layers, wherein each layer can include continuous filaments or discontinuous fibers.

The term "natural material" refers herein to a material derived from plants, animals, insects or byproducts of plants, animals, and insects. Non-limiting examples of natural materials useful in the disposable articles include cellulosic fibers, cotton fibers, keratin fibers, silk fibers and the like. Non-limiting examples of cellulosic fibers include wood pulp fibers, hemp fibers, jute fibers, and the like. Non-limiting examples of keratin fibers include wool fibers, camel hair fibers, and the like.

The term "thermoplastic magnetic material" refers herein to a composite material comprising a substrate with a one or more thermoplastic magnetic members disposed thereon.

The term "thermoplastic magnetic member" refers herein to a thermoplastic material with magnetic particles dispersed therethrough.

Thermoplastic Magnetic Members

As noted above, a thermoplastic magnetic member is a thermoplastic material having magnetic particles dispersed therethrough. As is well known, a thermoplastic material softens or even melts when exposed to heat. Such behavior facilitates manufacture of the personal care articles and thermoplastic magnetic members described herein and the method of production thereof, also discussed herein.

Suitably, a thermoplastic magnetic member of the present invention comprises between about 5% and about 60% of a thermoplastic material, preferably between about 10% and about 50%, more preferably between about 10% and about 25% of a suitable thermoplastic material as discussed below. The thermoplastic magnetic member also comprises between about 40% and about 95% of a thermoplastic material, preferably between about 50% and about 90%, of a suitable magnetic particulate material as described below. The member may also comprise minor amounts of other materials known in the art for inclusion in compositions of a thermoplastic material, such as plasticizers, antioxidants, colorants and the like.

Thermoplastic Materials

Suitable thermoplastic materials include those that become sufficiently fluid upon heating to allow incorporation of magnetic particulate material, for example, by extrusion mixing, kneading in a sigma mixer, or by other suitable means.

In some embodiments, at least a portion of the thermoplastic material may comprise a material with substantially plastic properties. Exemplary classes of materials include, but are not limited to polyolefins, polyamides, polyacetals, polyethers, polyesters, polyurethanes, and poly(meth)acrylates. Particularly preferred are polyolefins. A particularly preferred polyolefin is a polypropylene resin having a melt flow rate greater than about 100 g/10 min as measured according to ASTM standard method 1238. Commercially available resins that are suitable for use as a thermoplastic component of the present invention include a high melt flow rate polypropylene available from Basell Polyolefins, Inc. of Hoofddorp, Netherlands as PRO-FAX SC973 and a polypropylene homopolymer available from ExxonMobil Chemical of Houston, Tex. as PP3546G.

In some embodiments at least a portion of the thermoplastic material may comprise a thermoplastic elastomer. Such compositions comprise thermoplastic elastomers selected from the group consisting of styrenic block copolymers, metallocene-catalyzed polyolefins, polyesters, polyurethanes, polyether amides, and combinations thereof. Suitable styrenic block copolymers may be diblock, triblock, tetrablock, or other multi-block copolymers having at least one styrenic block. Exemplary styrenic block copolymers include styrene-butadiene-styrene, styrene-isoprene-styrene, styrene-ethylene/butylenes-styrene, styrene-ethylene/propylene-styrene, and the like. Commercially available styrenic block copolymers include KRATON from the Shell Chemical Company of Houston, Tex.; SEPTON from Kuraray America, Inc. of New York, N.Y.; and VECTOR from Dexco Chemical Company of Houston, Tex. Commercially available metallocene-catalyzed polyolefins include EXXPOL and EXACT from ExxonMobil Chemical of Baytown, Tex.; and AFFINITY and ENGAGE from Dow Chemical Company of Midland, Mich. Commercially available polyurethanes include ESTANE from Noveon, Inc., Cleveland, Ohio. Commercially available polyether amides include PEBAX from Atofina Chemicals of Philadelphia, Pa. Commercially available polyesters include HYTREL from E.I. DuPont de Nemours Co., of Wilmington, Del.

Particulate Magnetic Material

The other key component of the thermoplastic magnetic member of the present invention is a particulate magnetic material. Suitable magnetic particulate materials include but are not limited to magnetoplumbite-structure ferrite particles and/or rare-earth magnet particles with an average particle diameter between about 0.5 and about 1.5 microns which exhibit a surface magnetic flux density of not less than 2000 Gauss after incorporation into the thermoplastic magnetic member. Preferably, the magnetic flux density is greater than about 3000 Gauss, more preferably greater than about 5000 Gauss. Commercially available materials include magnetoplumbite-structure ferrite particles, such as GP-300 available from Toda Kogyo Corporation of Hiroshima, Japan; HM410 available from Hoosier Magnetics Inc. of Ogdensburg, N.Y.; and rare-earth magnetic particles such as MQP-B available from Magnequench Co., Ltd. of Indianapolis, Ind. or the like. A particularly preferred material is a strontium-ferrite powder available from AMC Magnet Co. Ltd. of Anhui, China as BMS-5.

Method of Making Thermoplastic Magnetic Materials

The above magnetic materials can be manufactured by a process 50 of the present invention, one embodiment of which is illustrated schematically in FIG. 1. The thermoplastic magnetic members can be deposited onto the substrate through a variety of means suitable for supplying and depositing molten thermoplastic resins. The means could include ink jet, spraying, coating, screen-printing, intaglio printing, flexographic printing, and the like. In the preferred embodiment of the present invention, the means of supplying and depositing molten thermoplastic resins can be provided by a rotogravure printing process because it provides flexibility in desired x-y-z dimensions of the thermoplastic member and desired quantity of deposition of the molten thermoplastic resin.

FIG. 1 shows a first substrate 36, which can be provided by a supply roll 52, moving through a rotogravure printing device 54 that deposits a molten blend of a suitable thermoplastic material and magnetic particles as described herein onto printing device 54 so as to form thermoplastic magnetic members 60 for deposition onto the first substrate 36. Optionally, a second substrate 34, which can be provided by a supply roll 56, can be combined with the first substrate 36 to cover the thermoplastic magnetic member 60 while it is still in a molten or semi-molten state to allow the molten thermoplastic magnetic member 60 to form an adequate bond strength with the second substrate 34 (e.g., at least partially penetrate into and combine with the substrate for a fibrous substrate) to form one embodiment of a thermoplastic magnetic material 38. Thermoplastic magnetic members of the present invention can be also manufactured using similar processes using one or more webs comprising non-fibrous substrates such as films, foils, foams, and the like. Details of suitable processes are given in U.S. patent application Ser. Nos. 10/288,144, 10/429,433 and 11/087,345.

The molten blend may be prepared using any of the methods discussed above. Particularly preferred is compounding using a compounding twin screw extruder such as those available from Farrell Corporation of Ansonia, Conn. The molten blend is delivered to printing device 54 using any suitable means such as slot extrusion. A doctor blade (not shown) may be used to level the blend across the width of the printing device 54.

FIG. 2 is a magnified view of a rotogravure pattern 70 for formation of a thermoplastic magnetic member 60. As shown, cells 71, 72 can be provided with differing diameters so as to control the x-y distribution of the molten blend of thermoplastic material and magnetic particles. It should also be recognized that the depth of any of the cells 71, 72 can be varied to control the z-dimension of thermoplastic magnetic member 60. It should also be recognized that the shape of gravure pattern 70 is substantially arbitrary and can be defined as needed for the final intended use of the thermoplastic magnetic material.

For substrates in a fibrous form, the degree of bond strength between thermoplastic magnetic member 60 and either or both of substrates 34, 36 can be controlled by applying a predetermined pressure at either or both of printing device 54 and roll pair 58 to affect the contact. As described above, the substrates 34 and 36 can be any suitable fibrous material. The source of the pressure can be any suitable means, including contacting or noncontacting means. FIG. 1 shows an example of a contacting means provided by a nip roll pair 58 which can be heated or chilled. Further, the degree of penetration into a fibrous substrate can also be affected by the viscosity of the molten thermoplastic magnetic member 60, the porosity of the fibrous substrates 34 and 36, and the surface tension of both the molten magnetic member 60 and the fibrous substrate. Suitably, the degree of penetration into a fibrous substrate is at least about two fiber diameters so as to insure adequate bonding with the substrate. The rotogravure-printing device 54 can be any suitable conventional thermal rotogravure device. One suitable rotogravure-printing device can be obtained from Roto-Therm Inc. of California.

When a substrate is in a non-fibrous form, the applied pressure as discussed above still has a substantial effect on bonding between the thermoplastic magnetic member 60 and the substrate because such pressure affects how completely the thermoplastic magnetic member contacts the surface of the web. Bond strength can be enhanced, however, through the use of bonding techniques as are known to the art. For example, thermal bonding (e.g., through the use of a heated embossed roll) can be used to remelt (or partially remelt) either or both of thermoplastic magnetic member 60 and substrate(s) 34, 36 so as to increase bonding therebetween. As will be recognized, the energy for such thermal bonding can also be provided by sources in addition to a heated roll. Examples include ultrasonic bonding (see e.g., U.S. Pat. No. 4,823,783) and RF (i.e., microwave) heating. Also suitable is dynamic mechanical bonding as described in U.S. Pat. No. 4,854,984 where the layers to be bonded are forwarded in a face-to-face relation through a pressure-biased nip between a patterned nip-defining member and an opposing nip-defining member (e.g., a relief-patterned cylinder and an anvil cylinder) which members are independently driven to maintain a predetermined surface velocity differential between them. It should also be recognized that each of these bonding methods is also suitable for use with a fibrous substrate when the fibrous substrate comprises thermoplastic fibers.

Uses of Thermoplastic Magnetic Members

The thermoplastic magnetic members of the present invention can be utilized in various articles of wear and use requiring a closure system for holding the articles in place on the wearer or for providing barrier properties in packaging including such articles as lotioned wipe or tissue dispensers. Such articles may be either disposable or durable. Some examples of articles utilizing the closure system of the present invention are illustrated in FIGS. 3-10.

Absorbent Article Component

When used as a component of a disposable absorbent article, the thermoplastic magnetic members of the present invention provide resistance to other products that are often used in conjunction with such absorbent articles so as to maintain the functionality of the closure system of the absorbent article even if a surface of the closure system becomes contaminated. For example, baby lotion is frequently used in conjunction with changing an infant diaper. If the surface of an adhesive closure system becomes contaminated with such baby lotion, adhesive functionality may be substantially lost. On the other hand, magnetic attraction is not substantially diminished by a thin layer of baby lotion on the surface of a thermoplastic magnetic member so that little, if any, loss of functionality of a closure system based on the thermoplastic magnetic members described herein would b expected.

Figure 3:
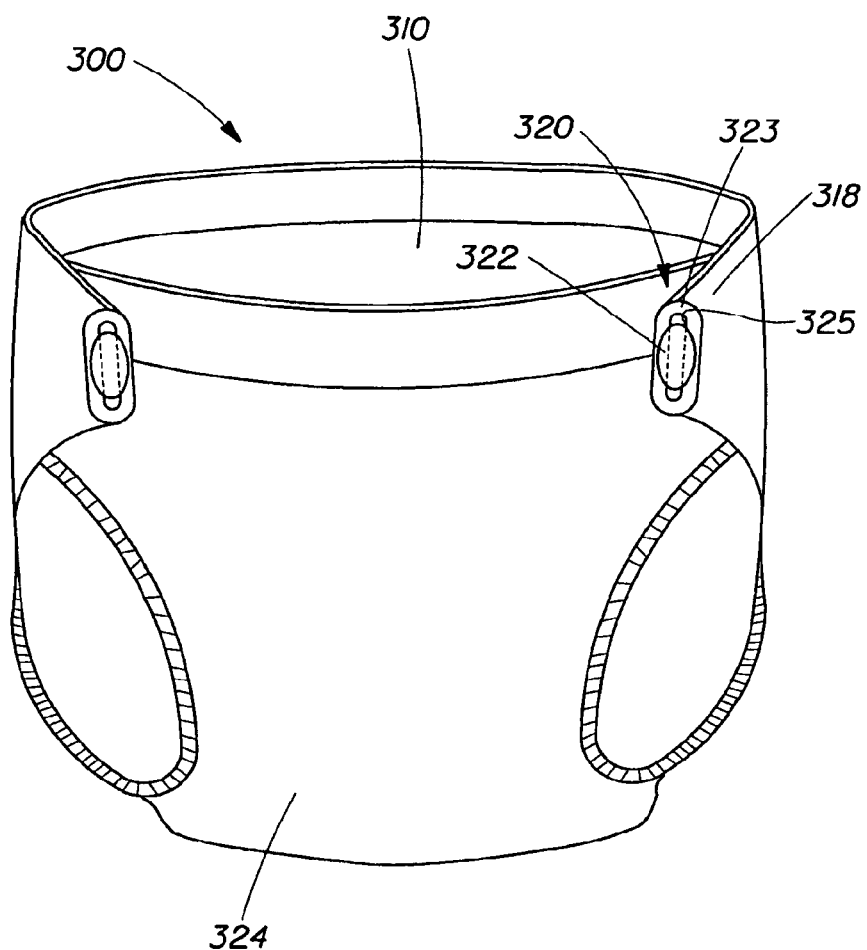
FIG. 3 is an isometric view a disposable absorbent article, a diaper, having a closure system using a thermoplastic magnetic member according to the present invention.

FIG. 3 shows an isometric view of a diaper 300 having waist opening 310 with a combination mechanical/magnetic closure system 320. As will be recognized, waist opening 310 is formed when closure system 320 is in a closed configuration as shown in FIG. 3. In this embodiment of the present invention, the closure system 320 comprises a matched pair of thermoplastic magnetic members 322, 323. The magnetic functionality resists normal forces that would tend to cause closure system 320 to open and the mechanical functionality provides a resistance to shear forces that would cause the closure system 320 to open. The magnetic functionality has the additional benefit of causing the two components 322, 323 of closure system 320 to be self-aligning.

In the embodiment of diaper 310 shown in FIG. 3, closure system 320 is disposed on side panel 318. A convenient means of providing such a structure is to print a thermoplastic magnetic member so as to form a first thermoplastic magnetic member which serves as first closure component 322 on the nonwoven material forming the outer layer of side panel 318 using the method described above. The complementary thermoplastic magnetic member which serves as second closure component 323 can be printed on the nonwoven portion of backsheet 324 (if it is a cloth-like backsheet) or printed on the film itself.

As can be seen most clearly in FIG. 3, closure system 320 comprises a matched set of thermoplastic magnetic members, first closure component 322 and second closure component 323. First closure component 322 comprises a three dimensional thermoplastic magnetic member having a rounded rectangular footprint. Second closure component 323 has a similar footprint to that of component 322 except that second closure component 323 is provided with an aperture 325. When closure system 320 is in a closed configuration, first closure component 322 is inserted in aperture 325. In this configuration, the magnetic properties of first and second closure components 322, 323 provide resistance to normal forces tending to cause closure system 320 to open. Similarly the inserted relationship between first closure component 322 and aperture 325 provide resistance to lateral forces tending to cause closure system to open. If desired, closure system can be provided with features to encourage the components to be self aligning. For example, in one embodiment (not shown) the portion of aperture 325 that faces first closure component 322 could be provided with a tapered configuration causing aperture 325 to have the shape of a truncated cone. This wider opening at the point of insertion makes it easier for a caregiver to align first closure component 322 with aperture 325 when applying diaper 310. In another embodiment (not shown) aperture 325 could be provided with an oval or rounded rectangle configuration and first closure component 322 could be provided with a similar cross section so as to provide increased resistance to circumferential forces tending to cause closure system 320 to open. In yet another embodiment (not shown) a plurality of matched first closure components and apertures could be provided so as to provide a closure mechanism that is resistant to rotation. A closure system with such multiple closure component/aperture combinations has the additional advantage of allowing adjustability. It should also be recognized that a closure mechanism with opposing sets of first closure components on the individual components can provide similar resistance to lateral movement.

Thermoplastic magnetic members according to the present invention can also be used with tab and slot closure systems as described in U.S. Pat. No. 6,251,097 as an aid in aligning the components thereof.

In an alternative embodiment, not shown, the thermoplastic magnetic members of the present invention can form one or both of the primary fastening system and the waist closure system for providing side closure and waist closure respectively as described in greater detain detail in U.S. Pat. No. 5,151,092. The thermoplastic magnetic members have a particular advantage in that they can be designed so as to have "skin friendly" body contact surfaces and still provide a force serving to maintain a diaper in a closed configuration.

Figure 4:
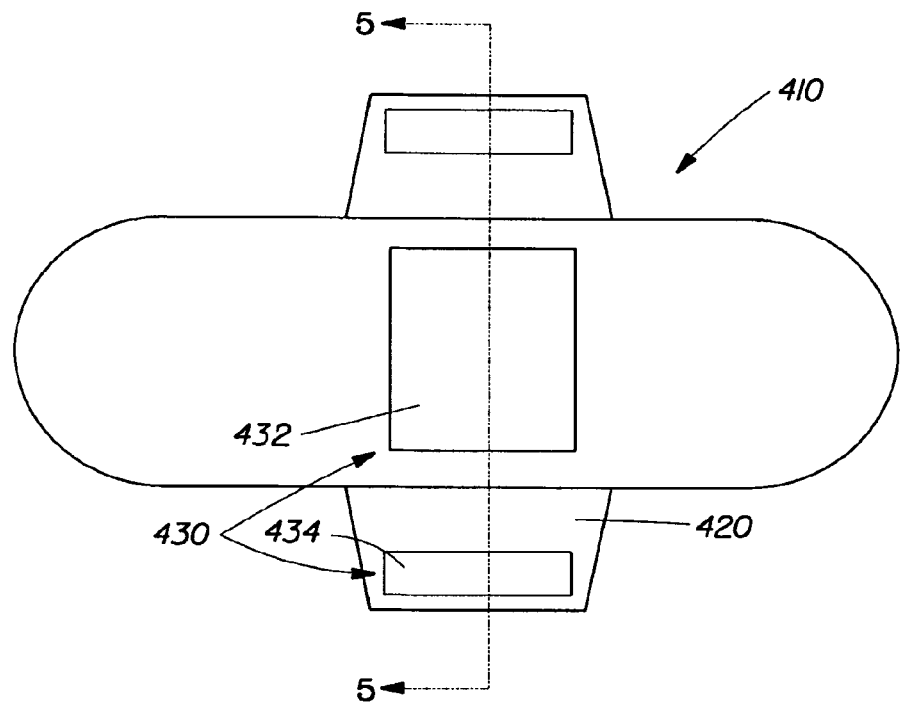
FIG. 4 is a bottom plan view of one embodiment of another disposable absorbent article, a catamenial pad, in an open configuration having wings comprising a closure system using a thermoplastic magnetic member according to the present invention.
Figure 5:
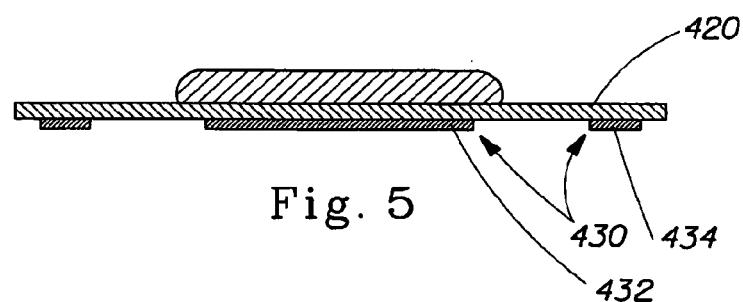
FIG. 5 is a cross sectional view taken along line 5-5 of the article shown in FIG. 3.
Figure 6:
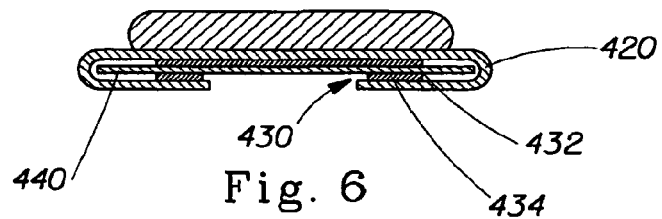
FIG. 6 is a cross sectional view of the article in FIG. 3 in a closed configuration wrapping a portion of an undergarment where the closure system of the present invention is used to secure the wings around the undergarment.

FIG. 4 shows a plan view of a feminine sanitary napkin 410 with wings 420, having a magnetic closure system 430 using thermoplastic magnetic members according to the present invention disposed on the garment surface thereof (shown most clearly in FIG. 5). In this embodiment of the present invention, the magnetic closure system 430 allows a user to reposition the sanitary napkin 410 on her undergarment without substantial loss of adhesion as may occur when using sanitary napkins provided with panty fastening adhesive according to the prior art.

In this embodiment of the present invention, closure system 430 comprises a matched set of a chassis thermoplastic magnetic member 432 and a pair of wing thermoplastic magnetic members 434 disposed on the wings 420. As shown most clearly in FIG. 6, in use, the wings wrap the crotch region of a wearer's undergarment 440 so as to hold sanitary napkin 410 in a position to protect the undergarment from staining by menses.

It should be noted that a plurality of absorbent articles comprising the thermoplastic magnetic members described above can be provided with suitable packaging so as to provide an article of commerce for such personal care articles. It is believed that, when such an article of commerce is provided, the thermoplastic magnetic members discussed herein are more resistant to the damaging effects of compression packaging as is typically used for disposable absorbent articles. For example, compressive forces may cause reduction in the loft of the loop portion of a hook and loop fastening system causing a reduction in the efficiency thereof. Similarly, compressive packaging may cause increased adhesive forces between an adhesive member and a release liner associated therewith, thereby increasing the difficulty of separating the adhesive from the release liner.

Component of Durable and Non-Durable Consumer Goods

Figure 7:
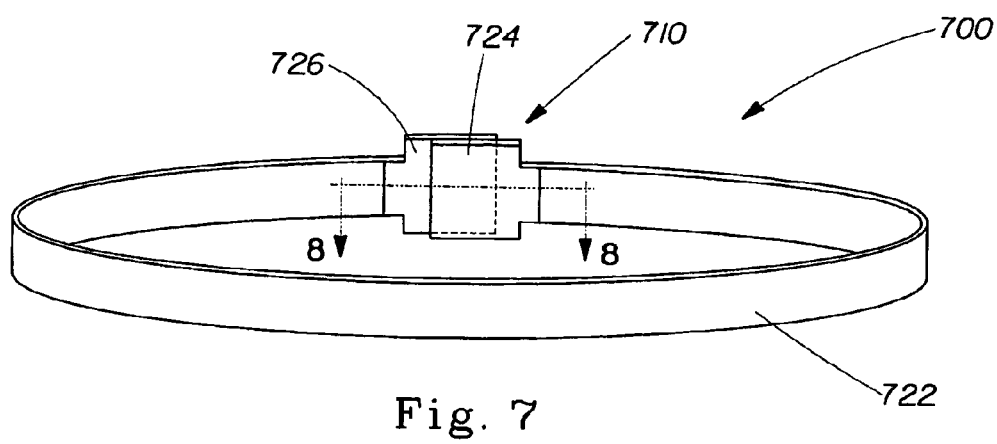
FIG. 7 is an isometric view of one embodiment of a body wrap or belt having a magnetic closure system comprising a thermoplastic magnetic member of the present invention.

FIG. 7 shows a perspective view of magnetic wrap 700 with a closure system 710 comprising substrate 722 and a matched set comprising first and second thermoplastic magnetic members 724, 726. In this embodiment, the thermoplastic magnetic members 724, 726 have a three dimensional configuration with a profile in the z-direction which mechanically interlocks to resist lateral movement thereof (shown most clearly in FIG. 8.).

Figure 8:
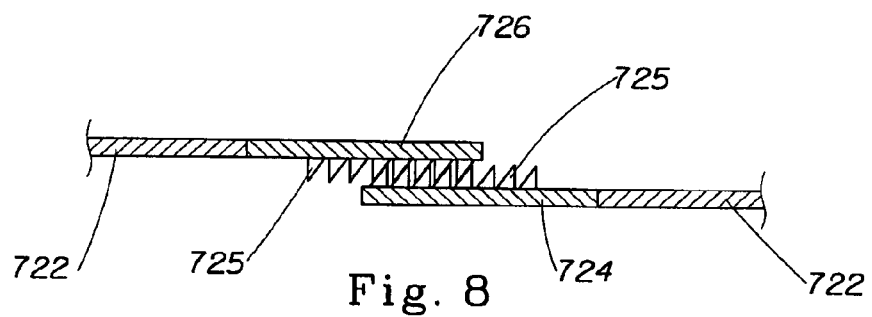
FIG. 8 is a top view taken along line 8-8 of FIG. 7 showing a three dimensional thermoplastic magnetic member according to the present invention.

FIG. 8 is a top view of wrap 700 along line 8-8. Substrate 722 can be a fibrous material (nonwoven, woven, knit, paper and the like) or a non-fibrous material such as a film which may optionally be provided with apertures (e.g., using hydroforming technology). The substrate may also comprise a laminate of one or more of these materials. Wrap 700 also comprises a matched set of thermoplastic magnetic members 724, 726 associated with the substrate 722. In this embodiment of closure system 710 shown herein, thermoplastic magnetic members 724 and 726 have a uniform configuration with a plurality of projections 725 providing a profile in the z-direction. As can be seen in FIG. 8, projections 725 on each of the opposing thermoplastic magnetic members 724, 726 mechanically engage so as to resist lateral movement of the thermoplastic magnetic members relative to each other. In the simplest embodiment, each thermoplastic magnetic member can have only a single projection forming a raised mechanical stop so as to resist such lateral movement. As can also be seen, differing numbers of projections 725 may be engaged so as to provide adjustability to wrap 710 for fitting various body sizes.

While the projections 725 are shown in FIG. 8 as having a triangular cross section, it should be recognized that projections with any cross section suitable for resisting lateral movement may be used. For example, such projections could have rectangular, irregular or other cross sections as one of ordinary skill would recognize as being suitable for resisting lateral movement.

Figure 9:
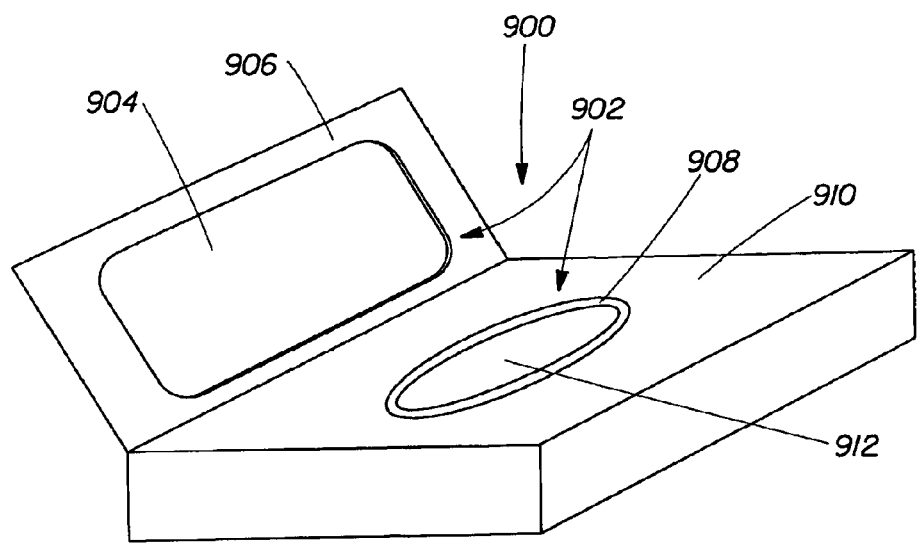
FIG. 9 is an isometric view of one embodiment of a package having a closure system comprising a thermoplastic magnetic member of the present invention.

FIG. 9 shows package 900 for a personal care product (e.g., tissues or wet wipes) having a magnetic closure system 902 comprising a first thermoplastic magnetic member 904 associated with a lid 906, and a second thermoplastic magnetic member 908 associated with a dispensing face 910 around a dispensing opening 912. By providing thermoplastic magnetic members 904 and 908 with opposite polarities attraction, and closure of the lid when desired may be insured. The normal force provided by the magnetic field can be sufficient to provide a desired functional holding force between the lid 906 and dispensing face 910 so as to minimize evaporation of any liquid materials contained in package 900 (e.g., from a lotion if the personal care product is a wet wipe). Contrary to adhesive-based closure systems of the prior art, this closure force will continue to be effective even in the presence of contamination adjacent opening 912 such as from lotion from a wet wipe personal care product.

Figure 10:
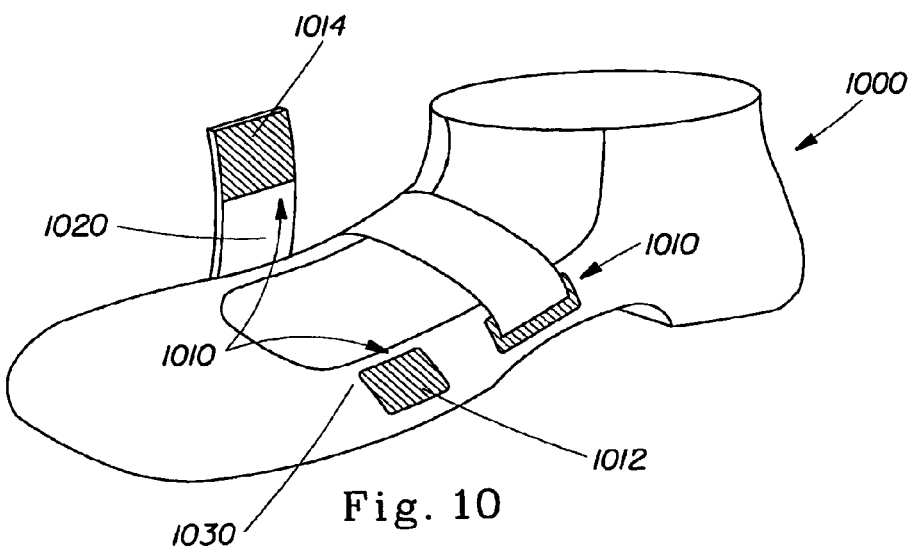
FIG. 10 is an isometric view showing a shoe with a closure system comprising a three dimensional thermoplastic magnetic member according to the present invention.

FIG. 10 shows a durable goods embodiment of the present invention where a matched set of thermoplastic magnetic members are used to provide a closure mechanism 1010 for an article suitable for wear by an individual, shoe 1000. As can be seen in FIG. 10, closure mechanism 1010 is shown in both an open and a closed configuration. As can be seen most clearly in the open configuration, closure mechanism 1010 comprises fixed clasp 1012 which is attached to the vamp 1030 of shoe 1000 and movable clasp 1014 which is attached to strap 1020. Clasps 1012 and 1014 comprise a matched set of thermoplastic magnetic members having a design very similar to that shown in FIG. 8 whereby a series of three dimensional protrusions provides mechanical interlocking to resist lateral forces tending to cause closure mechanism 1010 to open while the attractive magnetic forces resulting from the opposed polarities of clasps 1012 and 1014 provide resistance against normal forces tending to cause closure mechanism 1010 to open. As will also be recognized by comparing clasps 1012, 1014 to the closure mechanism 710 of FIG. 8, tension in strap 1020 may be adjusted by engaging different numbers of the protrusions.

Closure mechanism 1010 may be manufactured by disposing the thermoplastic magnetic member which will ultimately become movable clasp 1014 on a fibrous substrate which will ultimately become a part of strap 1020 using the method described above. The thermoplastic magnetic member which forms clasp 1012 may also be formed on a substrate as described above and either adhesively joined to the vamp of shoe 1000 or, if desired, the substrate on which clasp 1012 has been disposed may be used as a material for production of shoe 1000.

The dimensions and values disclosed herein are not to be understood as being strictly limited to the exact numerical values recited. Instead, unless otherwise specified, each such dimension is intended to mean both the recited value and a functionally equivalent range surrounding that value. r example, a dimension disclosed as "40 mm" is intended to mean "about 40 mm".

All documents cited in the Detailed Description of the Invention are, in relevant part, incorporated herein by reference; the citation of any document is not to be construed as an admission that it is prior art with respect to the present invention. To the extent that any meaning or definition of a term in this written document conflicts with any meaning or definition of the term in a document incorporated by reference, the meaning or definition assigned to the term in this written document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

The invention claimed is:

1. A disposable absorbent article comprising a closure system comprising at least one thermoplastic magnetic member, said thermoplastic magnetic member comprising a thermoplastic material having magnetic particles dispersed therethrough, wherein said thermoplastic material comprises:
   a resin selected from the group consisting of polyolefins, thermoplastic elastomers, polyamides, polyacetals, polyethers, polyesters, polyurethanes, poly(meth)acrylates, and compatible mixtures thereof; and
   said magnetic particles are selected from the group consisting of magnetoplumbite-structure ferrite particles, rare-earth magnet particles, and mixtures thereof;
   wherein said thermoplastic material is present in an amount of from about 10% to about 25% and said magnetic particles are present in an amount of from about 50% to about 90%;
   wherein at least a portion of the thermoplastic material comprises a thermoplastic elastomer selected from the group consisting of styrenic block copolymers, metallocene-catalyzed polyolefins, polyesters, polyurethanes, polyether amides, and combinations thereof;
   wherein said thermoplastic magnetic member is deposited onto the surface of said disposable absorbent article by a rotogravure printing process, wherein the thermoplastic magnetic member partially penetrates into and combines with the disposable absorbent article.

2. The disposable absorbent article according to claim 1, wherein said closure system comprising at least one thermoplastic magnetic member comprises at least one matched pair of thermoplastic magnetic members comprising a first thermoplastic magnetic member and a second thermoplastic magnetic member, wherein said first thermoplastic magnetic member has a magnetic polarity opposite to a magnetic polarity of said second thermoplastic magnetic member, and wherein said first thermoplastic magnetic member and said second thermoplastic magnetic member are magnetically joined and mechanically interlocked when in a mated configuration.

3. The disposable absorbent article according to claim 1, wherein said disposable absorbent article is a disposable diaper.

4. A disposable absorbent article comprising a closure system comprising at least one matched pair of thermoplastic magnetic members comprising a first thermoplastic magnetic member and a second thermoplastic magnetic member, wherein the second thermoplastic magnetic member comprises an aperture, the first and second thermoplastic magnetic members each comprising a thermoplastic material having magnetic particles dispersed therethrough, wherein said thermoplastic material comprises:
   a resin selected from the group consisting of polyolefins, thermoplastic elastomers, polyamides, polyacetals, polyethers, polyesters, polyurethanes, poly(meth)acrylates, and compatible mixtures thereof; and
   the magnetic particles are selected from the group consisting of magnetoplumbite-structure ferrite particles, rare-earth magnet particles, and mixtures thereof,
   wherein the thermoplastic material is present in an amount of from about 10% to about 25% and the magnetic particles are present in an amount of from about 50% to about 90%;
   wherein at least a portion of the thermoplastic material comprises a thermoplastic elastomer selected from the group consisting of styrenic block copolymers, metallocene-catalyzed polyolefins, polyesters, polyurethanes, polyether amides, and combinations thereof,
   wherein said first thermoplastic magnetic member has a magnetic polarity opposite to a magnetic polarity of the second thermoplastic magnetic member, and wherein the first thermoplastic magnetic member and the second thermoplastic magnetic member are magnetically joined and mechanically interlocked when in a mated configuration, and
   wherein the first thermoplastic magnetic member is inserted into the aperture of the second thermoplastic magnetic member when in the mated configuration.

5. The disposable absorbent article according to claim 4, wherein said disposable absorbent article is a disposable diaper.

* * * * *